US010533941B2

(12) United States Patent
Strangi et al.

(10) Patent No.: US 10,533,941 B2
(45) Date of Patent: Jan. 14, 2020

(54) OPTICAL SENSOR PLATFORM EMPLOYING HYPERBOLIC METAMATERIALS

(71) Applicant: Case Western Reserve University, Cleveland, OH (US)

(72) Inventors: Guiseppe Strangi, Cleveland, OH (US); Kandammathe Valiyaveedu Sreekanth, Singapore (SG); Umut Gurkan, Cleveland, OH (US); Michael Hinczewski, Cleveland, OH (US); Mohamed Elkabbash, Cleveland, OH (US); Antonio De Luca, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 142 days.

(21) Appl. No.: 15/684,071

(22) Filed: Aug. 23, 2017

(65) Prior Publication Data
US 2018/0059020 A1    Mar. 1, 2018

Related U.S. Application Data

(60) Provisional application No. 62/378,464, filed on Aug. 23, 2016.

(51) Int. Cl.
*G01N 21/552*    (2014.01)
*G01N 33/543*    (2006.01)
(Continued)

(52) U.S. Cl.
CPC ...... *G01N 21/554* (2013.01); *B01L 3/502715* (2013.01); *B01L 3/502761* (2013.01);
(Continued)

(58) Field of Classification Search
CPC .............. G01N 21/554; G01N 21/553; G01N 21/7743; G01N 21/17; G01N 33/54373;
(Continued)

(56) References Cited

U.S. PATENT DOCUMENTS

2013/0293749 A1* 11/2013 Vaartstra ................ H04N 9/045
348/273

OTHER PUBLICATIONS

Sreekanth et al. "Large spontaneous emission rate enhancement in grating coupled hyperbolic metamaterials" Scientific Reports, Sep. 11, 2014 pp. 1-8. (Year: 2014).*
(Continued)

*Primary Examiner* — Michael L Hobbs
(74) *Attorney, Agent, or Firm* — Kaplan Breyer Schwarz, LLP

(57) ABSTRACT

Disclosed herein are optical sensor platform(s) employing hyperbolic metamaterial(s) supporting highly confined bulk plasmon guided modes over broad wavelength range(s) from visible to near-infrared. By exciting these modes using—for example—a two-dimensional (2D) grating-coupling technique, sensors according to the present disclosure advantageously exhibit extreme sensitivity modes up to a maximum of 30,000 nm per refractive index unit and a record figure of merit of 590 thereby permitting detection of ultralow-molecular-weight bio-molecules at picomolar concentrations.

9 Claims, 17 Drawing Sheets

(51) Int. Cl.
 *B01L 3/00* (2006.01)
 *G01N 21/77* (2006.01)
(52) U.S. Cl.
 CPC ....... *G01N 21/553* (2013.01); *G01N 21/7743* (2013.01); *G01N 33/54346* (2013.01); *G01N 33/54373* (2013.01); *B01L 2300/0654* (2013.01); *B01L 2300/0887* (2013.01)
(58) Field of Classification Search
 CPC ........... G01N 33/54346; G01N 33/487; G01N 33/483; B01L 3/502715; B01L 3/502761; B01L 2300/0887; B01L 2300/0654
 See application file for complete search history.

(56) References Cited

OTHER PUBLICATIONS

Kandammathe Valiyaveedu Sreekanth et al., "Enhancing the Angular Sensitivity of Plasmonic Sensors Using Hyperbolic Metamaterials, DOI: 10.1002/adom.201600448", "Advanced Optical Materials", dated Aug. 2, 2016, pp. 1767-1772, vol. 4, Publisher: Wiley-VCH Verlag GmbH & CO. KGaA, Weinheim.

Kandammathe Valiyaveedu Sreekanth et al., "Hyperbolic metamaterials-based plasmonic biosensor for fluid biopsy with single molecule sensitivity", dated 2017, DOI: 10.1051/epjam/2016015, "EPJ Applied Metamaterials", pp. 1-8, vol. 4, No. 1, Publisher: EDP Sciences.

* cited by examiner

OPTICAL SENSOR PLATFORM EMPLOYING HYPERBOLIC METAMATERIALS

CROSS REFERENCE TO RELATED APPLICATIONS

This application claims the benefit of U.S. Provisional Patent Application Ser. No. 62/378,464 filed 23 Aug. 2016 which is incorporated by reference as if set forth at length herein.

TECHNICAL FIELD

This disclosure relates generally to sensor technologies and more particularly to an optical sensor platform employing hyperbolic metamaterials.

BACKGROUND

As will be readily appreciated by those skilled in the art, optical sensor technologies offer significant opportunities in the chemical, environmental, biological and medical research and diagnostic field(s)—among others—particularly with respect to the detection of small numbers of molecules in highly dilute solutions. Given their potential importance, new and/or improved optical sensor technologies would represent a welcome addition to the art.

SUMMARY

An advance in the art is made according to an aspect of the present disclosure directed to an optical sensor platform employing hyperbolic metamaterials. In sharp contrast to contemporary optical sensor technologies and sensors constructed therefrom, optical sensors according to the present disclosure employ hyperbolic metamaterial(s) supporting highly confined bulk plasmon guided modes over broad wavelength range(s) from visible to near-infrared. By exciting these modes using—for example—a two-dimensional (2D) grating-coupling technique, a metalized methyl methacrylate structure, and/or a random distribution of nanoparticles, sensors according to the present disclosure advantageously detect ultralow-molecular-weight bio-molecules at picomolar concentrations.

BRIEF DESCRIPTION OF THE DRAWING

A more complete understanding of the present disclosure may be realized by reference to the accompanying drawing in which.

DETAILED DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the disclosure.

In the claims hereof any element expressed as a means for performing a specified function is intended to encompass any way of performing that function including, for example, a) a combination of circuit elements which performs that function or b) software in any form, including, therefore, firmware, microcode or the like, combined with appropriate circuitry for executing that software to perform the function. The invention as defined by such claims resides in the fact that the functionalities provided by the various recited means are combined and brought together in the manner which the claims call for. Applicant thus regards any means which can provide those functionalities as equivalent as those shown herein. Finally, and unless otherwise explicitly specified herein, the drawings are not drawn to scale.

Thus, for example, it will be appreciated by those skilled in the art that the diagrams herein represent conceptual views of illustrative structures embodying the principles of the disclosure.

Figure 1:
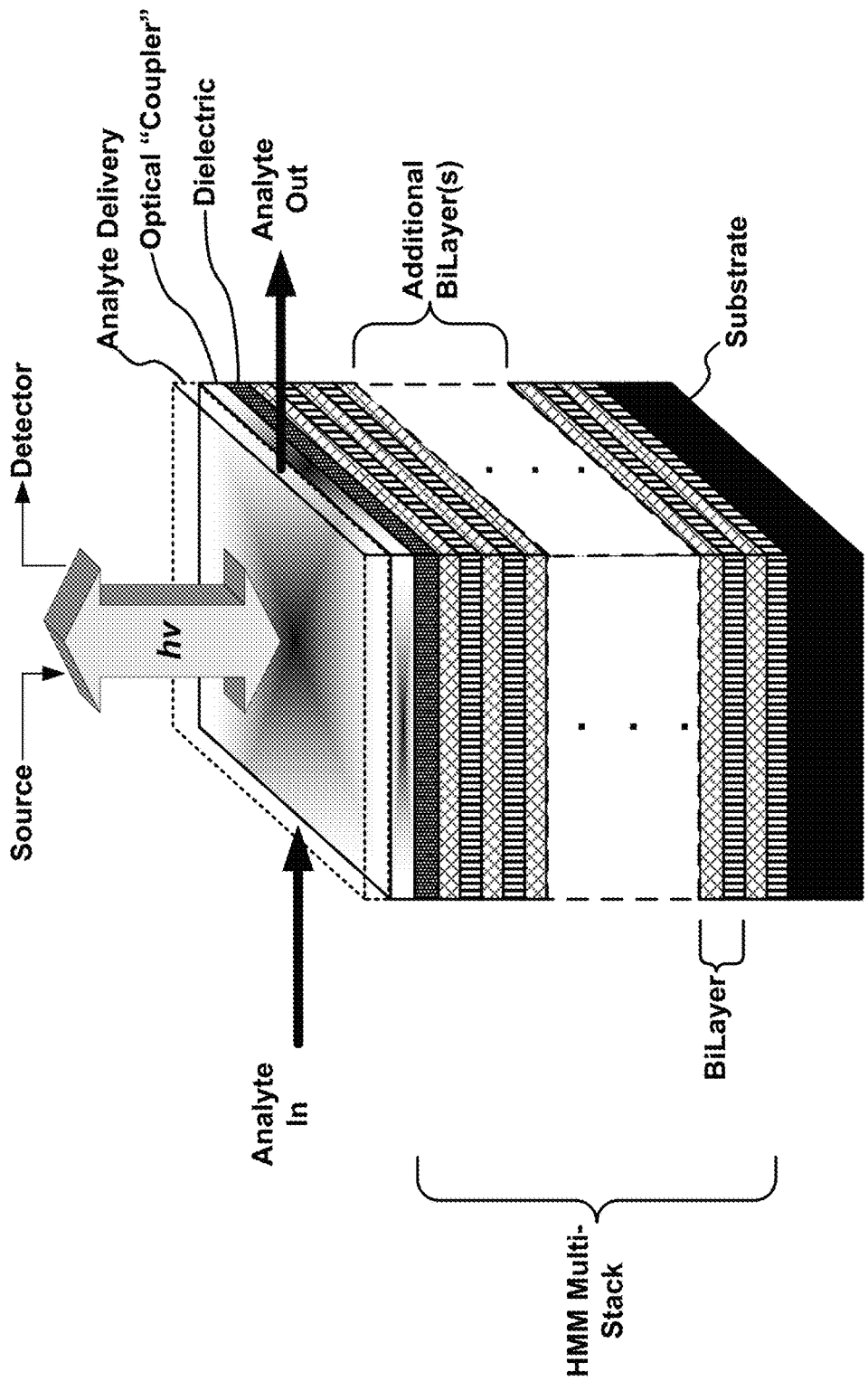
FIG. 1 shows a schematic of a generalized optical, hyperbolic metamaterial sensor (HMM) structure according to an aspect of the present disclosure.

FIG. 1 shows an illustrative generalized schematic of an optical hyperbolic metamaterial (HMM) sensor structure according to aspects of the present disclosure. As shown in that FIG. 1, a multi-stack hyperbolic metamaterial—comprising a number of bilayers (layer-pairs)—overlies a substrate. Overlying the HMM stack is a dielectric layer overlying which is an optical "coupler" structure. An analyte delivery structure overlies the coupler structure such that when light is directed thereupon, the presence of an analyte may be optically detected as a result of its effect upon surface plasmon/bulk plasmon interactions occurring within the HMM stack.

Figure 2:
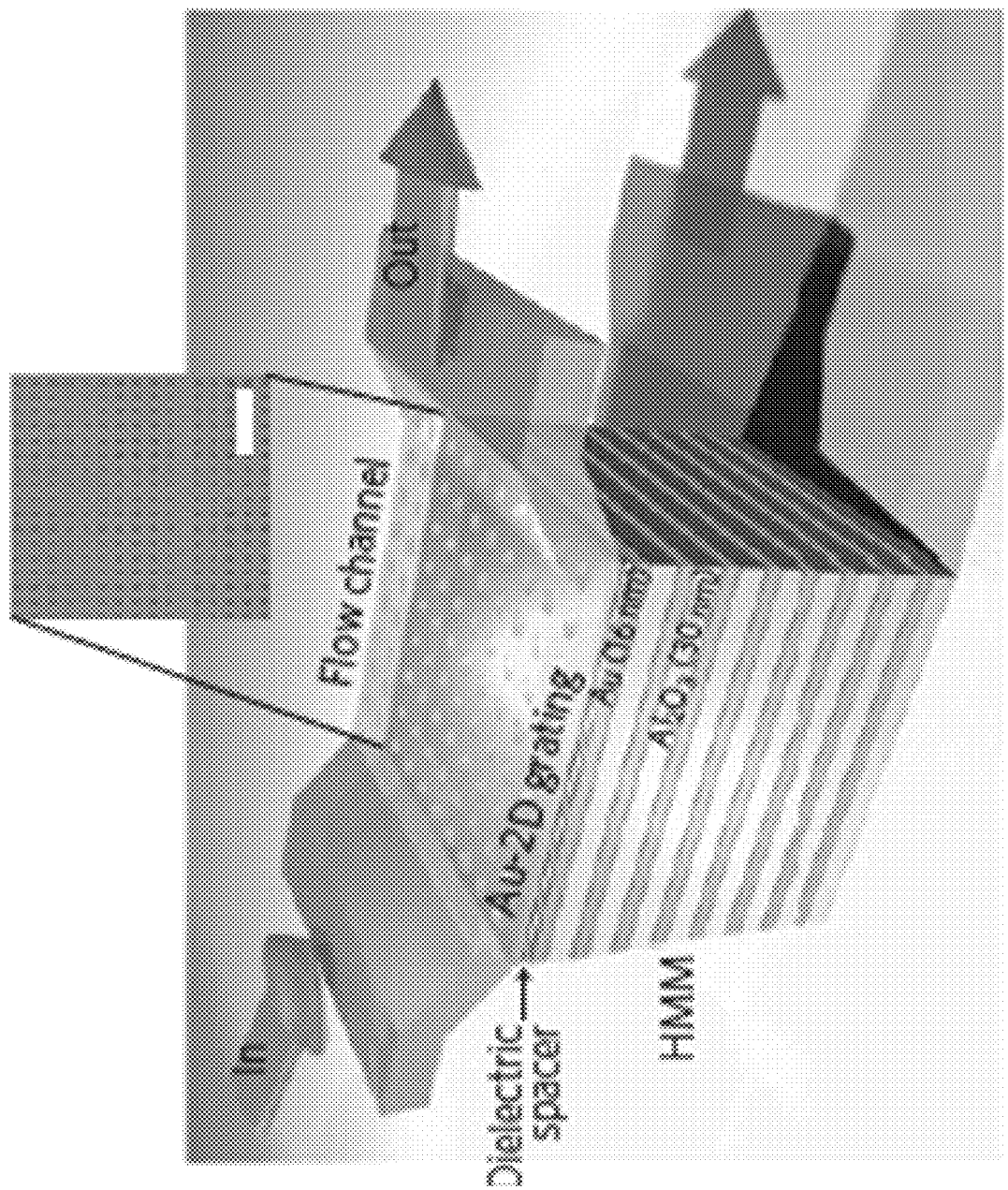
FIG. 2 shows a schematic of a 2D grating-coupled hyperbolic metamaterial (GC-HMM) sensor device including a fluid flow channel according to an aspect of the present disclosure.

Turning now to FIG. 2, there is shown a schematic of an illustrative, fabricated, miniaturized GC-HMM sensor device according to an aspect of the present disclosure. As may be observed from that FIG. 2, the illustrative GC-HMM sensor device includes a microfluidic flow channel overlying a grating coupled metamaterial.

Illustratively, the metamaterial shown includes a stack of eight (8) Au/Al$_2$O$_3$ layer-pairs. Overlying the eight layer-pair stack is a dielectric spacer layer which in turn is overlaid with a Gold, 2-Dimensional (Au-2D) grating. As noted previously, the microfluidic flow channel overlies the Au-2D grating in this illustrative sensor structure.

With continued reference to FIG. 2, it is noted that the layer-pair stack is shown including eight layer-pairs. Advantageously, structures according to the present disclosure (as shown schematically in FIG. 1) may include a fewer number or greater number of layer-pairs. Additionally, it may be observed that an individual Au layer and an individual Al$_2$O$_3$ layer—which together form an individual Au/Al$_2$O$_3$ layer-pair—are illustratively shown as 16 nm and 30 nm thick, respectively. Advantageously, the thicknesses of the individual layers of Au and Al$_2$O$_3$ may range from few nm (2-3) to tens of nanometers (30-50) such that the thickness of the metal-dielectric bilayer is deeply subwavelength (<$\lambda$/10).

The HMM structure may comprise a multistack of any metal-dielectric bilayers. More specifically, it is noted that while the individual layers are shown as comprising Au and Al$_2$O$_3$ respectively, structures according to the present disclosure may be fabricated from alternative materials as well. For example, the Au layers may be fabricated from Ag, Pd, Pt, Ti, and doped semiconductors, while the Al$_2$O$_3$ layers may be fabricated from any other suitable dielectric or oxide material.

As shown further in FIG. 2, a dielectric spacer layer overlies the layer-pair stack. This dielectric spacer layer may be advantageously formed from any of a variety of known dielectrics including poly-methyl-methacrylate (PMMA). While not specifically shown in FIG. 2, the dielectric spacer thickness may range from approximately 3 nm to several tens of nanometers.

Overlying the dielectric layer is a 2D subwavelength gold diffraction grating (Au-2D) having an average period of 500 nm and a hole size of 160 nm. Since the role of the diffractive grating is to couple the incoming radiation with the photonic nanostructure all range and varieties of periods and hole sizes can be designed and fabricated to match the relative optical momenta.

Overlying the Au-2D grating, is a microfluidic channel structure which provides a mechanism by which solutes (analytes) may be delivered and subsequently detected by the GC-HMM sensor structure. And while we have shown a fluidic (liquid) channel structure, those skilled in the art will readily appreciate that liquids and/or gases may be delivered and subsequently sensed by structures constructed according to the present disclosure.

Advantageously, and as will be readily appreciated by those skilled in the art, a GC-HMM sensor structure according to the present disclosure may be fabricated using well understood fabrication techniques and technologies. By way of illustrative example using the structure depicted in FIG. 2, a GC-HMM sensor structure according to the present disclosure may be fabricated by sequential deposition of 16 alternated layers of alumina (Al$_2$O$_3$) and gold (Au) thin films by using conventional electron beam and thermal evaporation techniques, respectively. All the thin films may be grown over micro-glass substrates with Al$_2$O$_3$ and Au pellets used as source materials.

Operationally, a solution including solute(s) to be detected enters an input of the microfluidic channel, flows across/within the GC-HMM, and subsequently exits an output. Due to its structure, the microfluidic channel restricts the solute mobility thereby facilitating its contact with the GC-HMM sensor structure. As a result of this contact, a number of the solute molecules are adsorbed onto the surface of the sensor structure. Advantageously, and with respect to bio-analytes—such a sensor platform has been shown to work well in both a flow-through mode as well as a batch mode (single injection of solute) since its ultrahigh sensitivity does not require an accumulation of large amounts of bio-analytes.

As the solution is injected or flows through the channel, light is directed thereupon and is diffused into two dimensions through the effect of the 2D grating which is illustratively fabricated from a thin Au layer having an array of spaced-apart holes formed therein. The incoming light—which is several hundreds of nanometers in wavelength—is directed onto and through the layers of the HMM which—as noted previously—illustratively includes 16 individual layers (8 layer-pairs) of reflective and conductive gold and transparent aluminum oxide and a dielectric. As a result, such light is "concentrated" into a very small volume much smaller than the wavelength(s) of light.

As this light strikes the HMM, it excites free electrons resulting in their oscillation and generation of a highly confined propagating surface wave—a surface plasmon polariton. This propagating surface wave in turn excites a bulk wave propagating across the sensor structure. The presence of the wave(s) results in strong, sharp dips in the spectrum of reflected light thereby generating a detectable effect. Advantageously, the combination of the surface plasmon and bulk plasmon waves excited through the eight bilayers (layer-pairs) result in remarkably sharp resonant modes which may then be employed to detect extremely small quantities of solute. Of further advantage, depending upon the size of the solute molecules, different amount(s) of frequency shift(s) or angular shift(s) are generated. The platform may be employed by using multiple read-out techniques: The reflectance of broadband light can be monitored for frequency shifts as function of the molecular binding events and/or for angular shifts of narrow banded (almost monochromatic) light.

Notably, and as will be readily appreciated by those skilled in the art—it is oftentimes desirable to detect molecular entities with great specificity. Advantageously, sensor devices according to the present disclosure may be made so specific through the use of one or more specific "trap" molecules. By way of illustrative example only, such trap molecules may include immobilized enzymes that may advantageously bind with specific substrates resulting in the enzyme-substrate combination being detected. The trap molecules may be so immobilized onto the top layer of the GC-HMM structure. Specific example of trap molecules, not exhaustive of all biomolecular interactions, may include biotin-avidin, antigen-antibodies, aptamers, multivalent biotinylated polymers, etc.—among others.

Figure 3A:
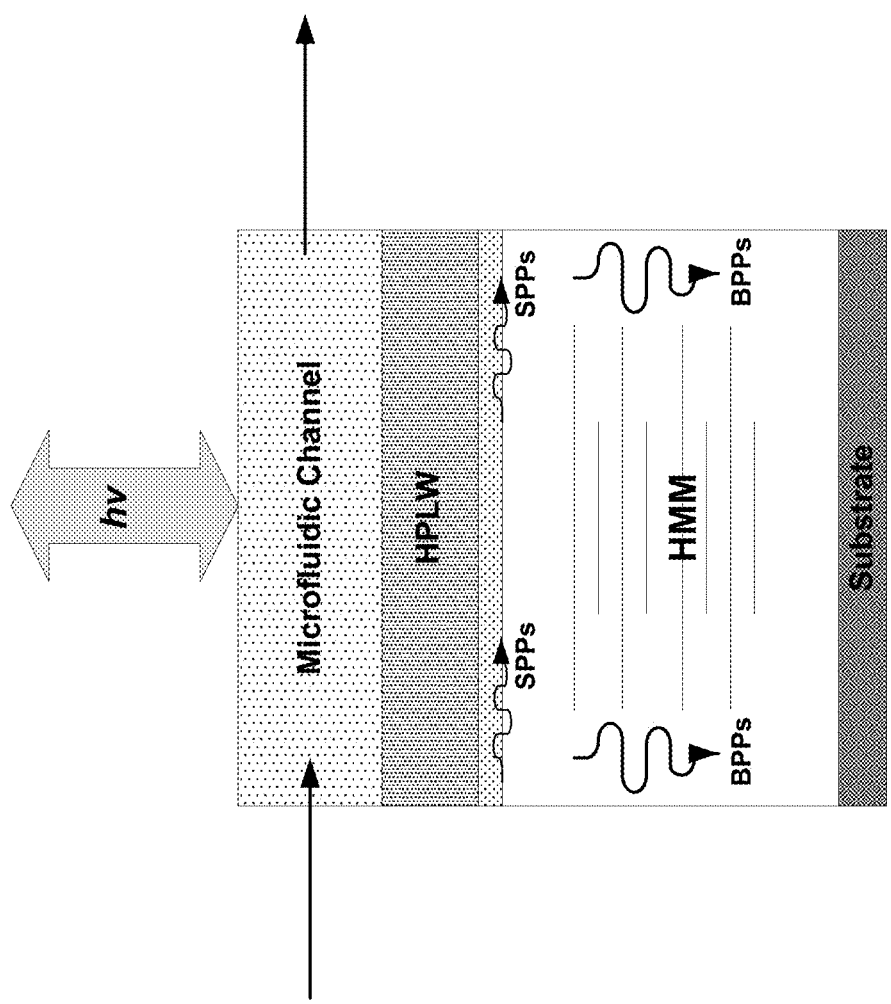
FIGS. 3(A)-3(C) show schematics of alternative HMM sensor device(s) that are fabricated in a lithography-free manner wherein 3(A) employs a hybrid partially leaky waveguide (HPLW) overlying the HMM stack; 3(B) employs a submicron layer of methyl methacrylate coated with a thin (5-15 nm) layer of metal (Au or Pd); and 3(C) employs a random distribution of nanoparticles—i.e., 100 nm $TiO_2$—all according to one or more aspects of the present disclosure.

Alternative embodiments of HMM sensor structures according to aspects of the present disclosure may be constructed using an innovative, lithographically free coupler positioned between incident radiation and the HMM structure. More particularly, and as schematically depicted in FIG. 3(A), such configurations may include a specific hybrid partly leaky waveguide (HPLW) overlying the HMM stack. Advantageously, with such a configuration, evanescent modes generated by the HPLW allow the coupling with highly confined modes of HMM structure thereby advantageously resulting in an efficient, ultrathin light coupler/decoupler.

Figure 3B:
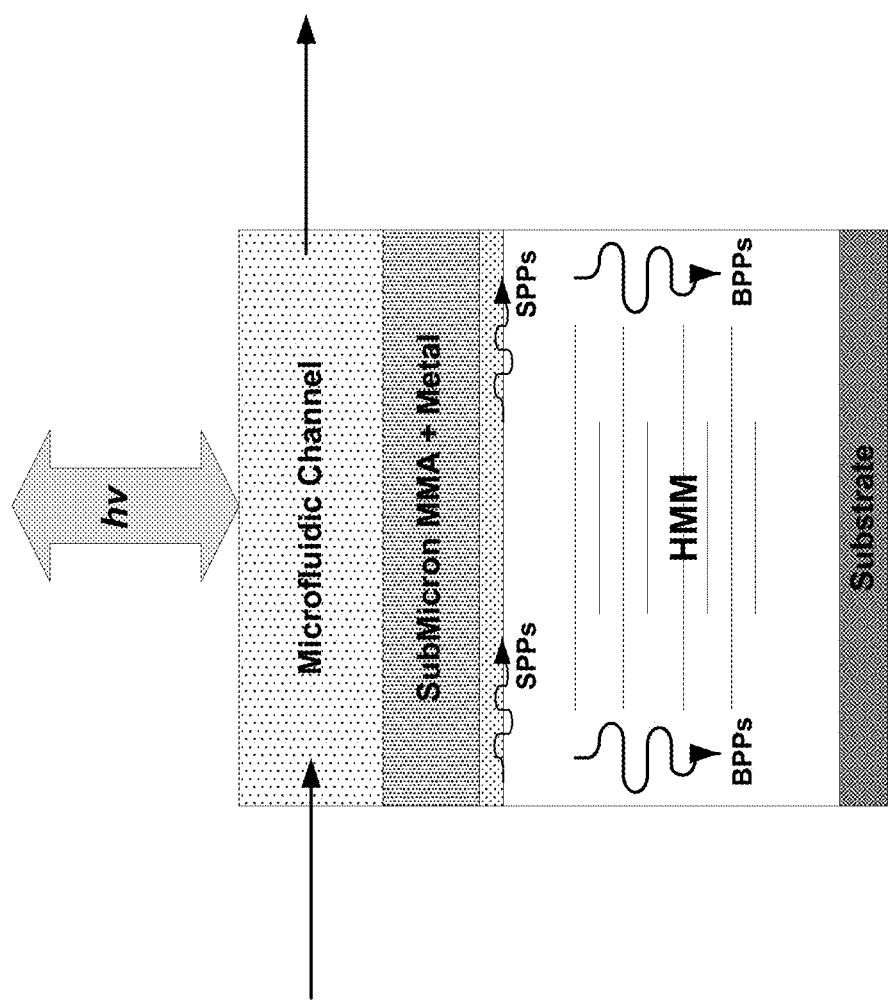
Figure 3C:
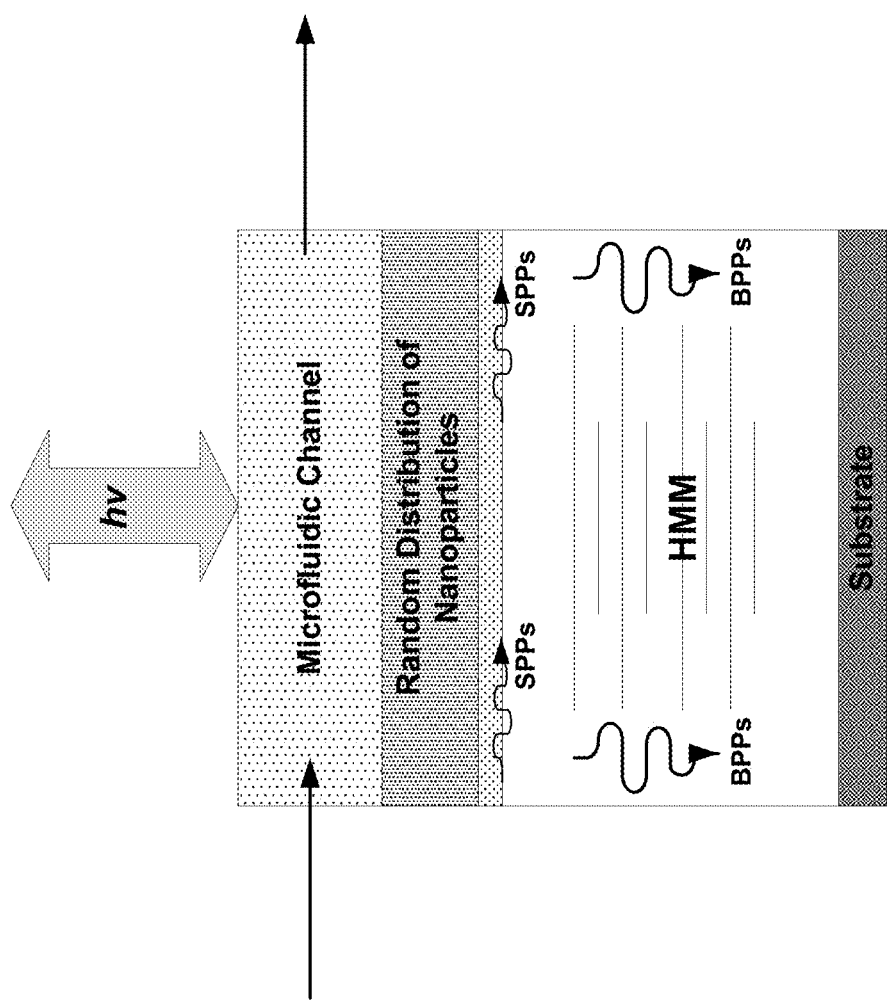

To explore the potential of a lithography-free HMM sensor, we experimentally replaced the earlier described grating-coupling mechanism with a waveguide coupler using submicron layer of methyl methacrylate (MMA) coated with a thin (5-15 nm) layer of metal (Au or Pd) (FIG. 3(B)) or by employing a random distribution of nanoparticles acting as "scatterers" to add momentum to the incoming light and to match the momenta of the bulk plasmon polaritons (FIG. 3(C)).

Figure 3D:
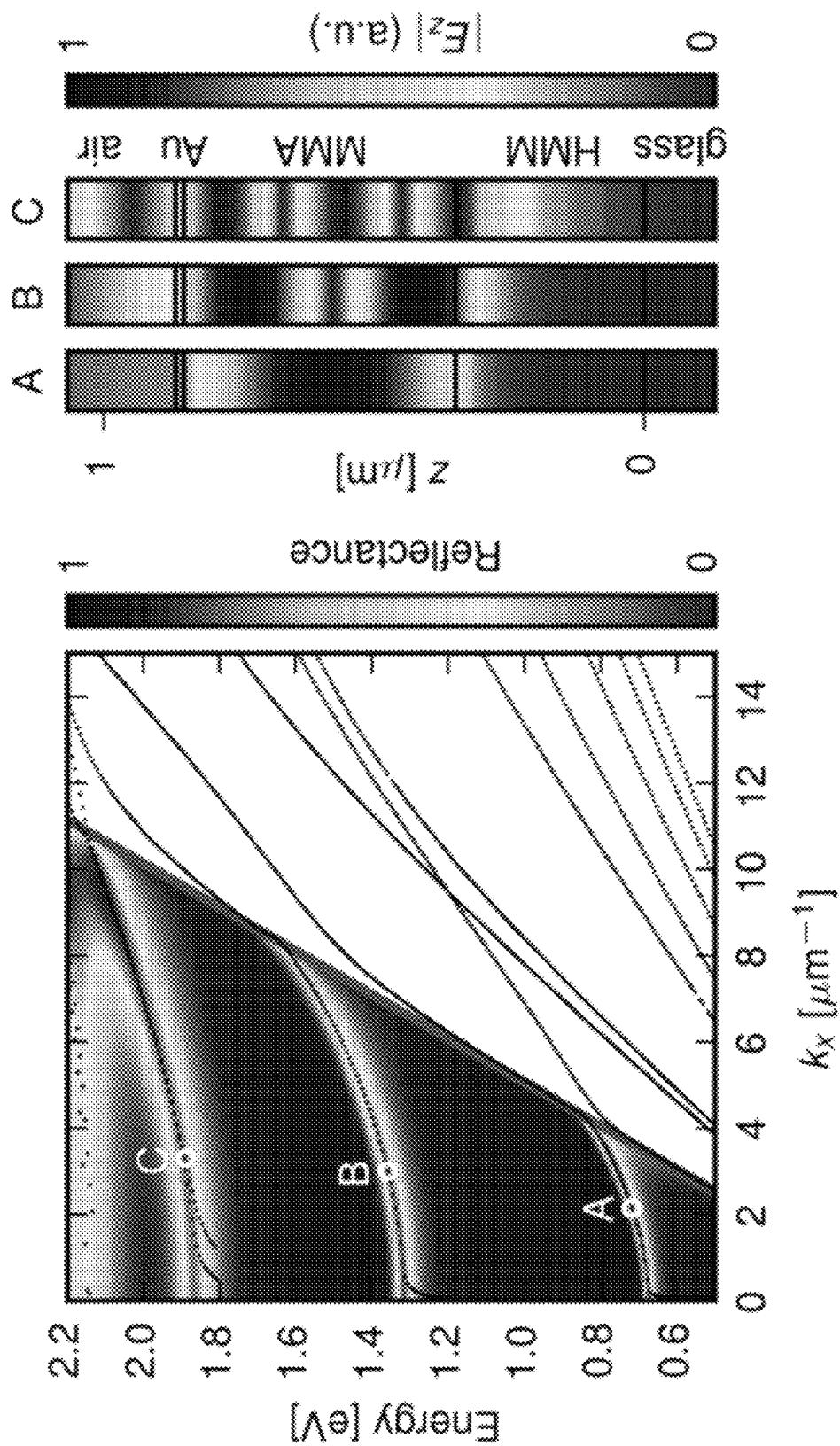
FIG. 3(D) shows (left) a theoretically calculated dispersion diagram for transverse magnetic modes (dotted lines) in a lithography-free HMM system in terms of photon energy versus momentum and (right) electric field magnitude for three modes located at A, B, C in left plot—according to aspects of the present disclosure.

FIG. 3(D) shows (left) a theoretically calculated dispersion diagram for transverse magnetic modes (dotted lines) in a lithography-free HMM system in terms of photon energy versus momentum and (right) electric field magnitude for three modes located at A, B, C in left plot—according to aspects of the present disclosure.

We note that with respect to the MMA coated with a thin metal, biomolecular detection studies with these alternative designs are ongoing, and we have already demonstrated the feasibility of the sensing mechanism in the context of hydrogen gas detection. By using Pd as the top metal layer, which can absorb $H_2$ from the surrounding medium, altering its dielectric properties, we can measure the shift $\Delta\lambda$ of the HMM mode in response to particular concentrations of $H_2$. These shifts are large, reproducible, and completely reversible when $H_2$ is removed from the environment. Moreover, we also have preliminary theoretical results for the lithography-free system that validate the novel optical coupling mechanism between incident radiation and the BPP modes in the HMM. The mode dispersion diagram (FIG. 3(D) left) of the system with an Au top layer (in the absence of functionalization and captured analytes) shows the presence of transverse magnetic modes that can be excited by incident photons from the superstrate, corresponding to sharply-defined minima in reflectance. The electric field profiles for three of these modes (FIG. 3(D) right) illustrate the coupling of the incoming radiation to BPP excitations.

Figure 3E:
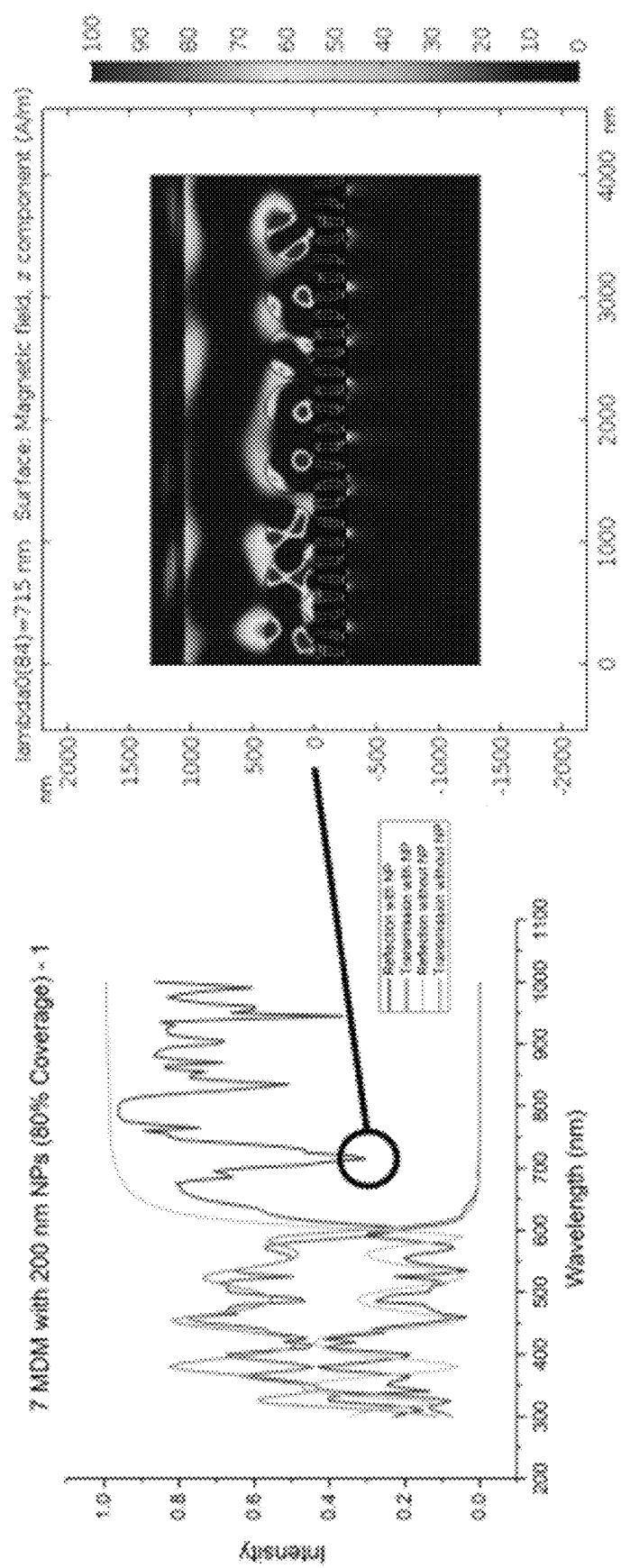
FIGS. 3(E)-3(J) show intensity vs wavelength graphs and corresponding magnetic field plots for structures including random distribution of nanoparticles according to aspects of the present disclosure.
Figure 3F:
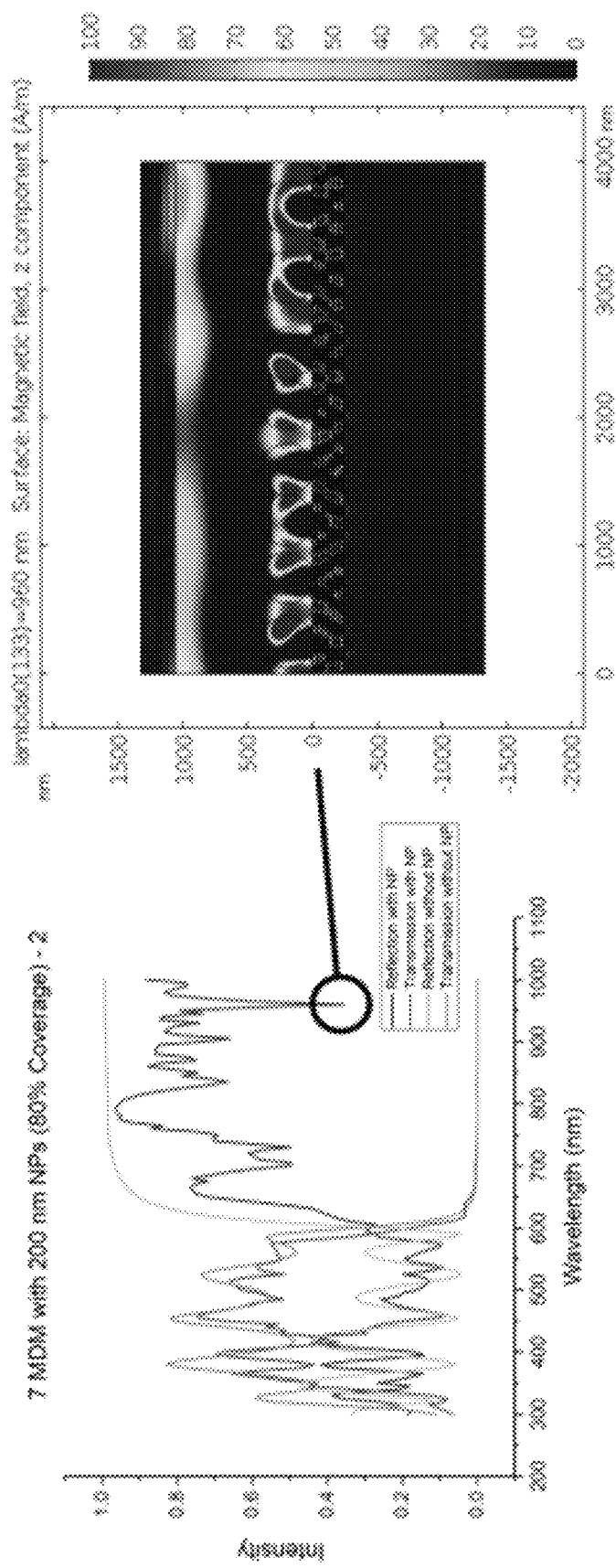
Figure 3G:
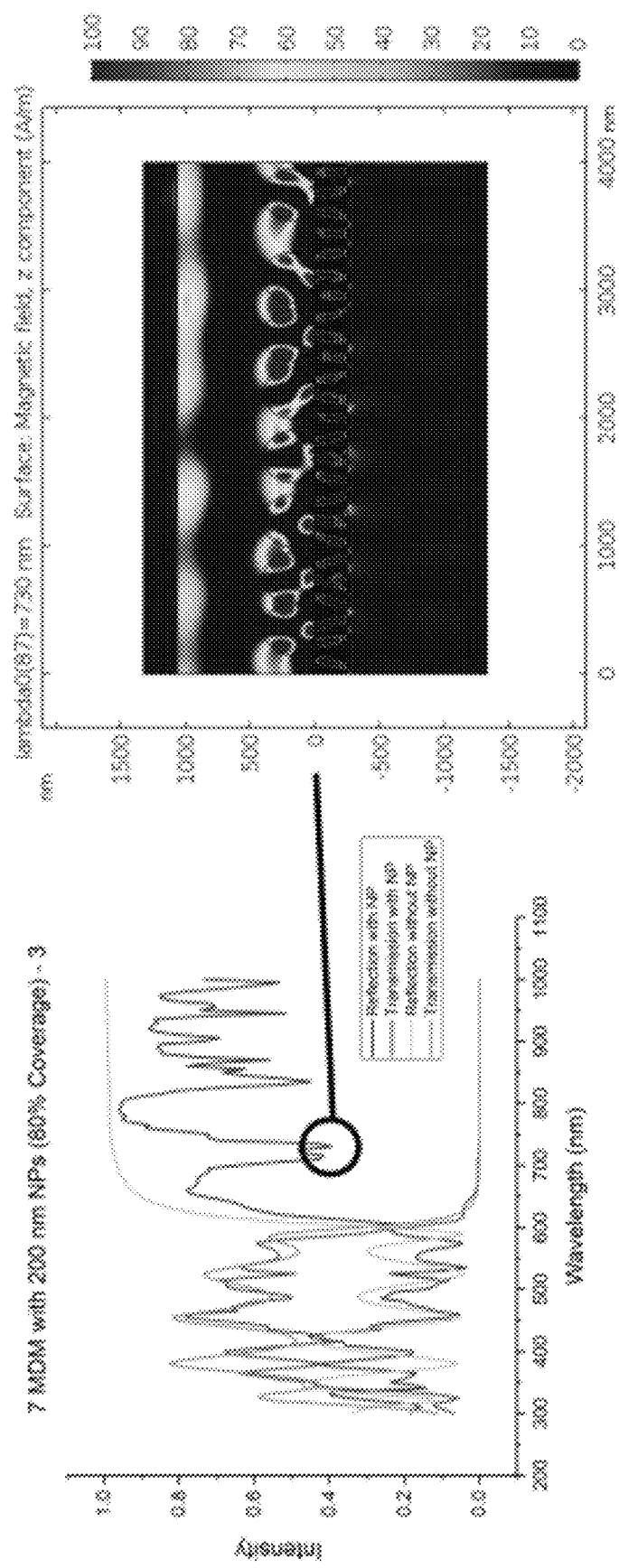

Large area lithography-free sensing areas were realized by depositing 100 and 200 nm $TiO_2$ nanoparticles with 60% and 80% coverage. The nanoparticles can be deposited by spin-coating or spray techniques. The percentage of coverage and NP size are two of the parameters that need to be controlled to couple the incoming radiation with the HMM nanostructure. With respect to HMM structures employing randomly-dispersed nanoparticles, we note that we have randomly dispersed 200 nm sized nanoparticles on the surface of the HMM with 80% linear coverage. We repeated this simulation with three different nanoparticle arrangements without changing the linear coverage, and in each of the three simulations, we noticed a dramatic increase in the strength of both surface and bulk plasmon coupling in the HMM. FIG. 3(E) right, FIG. 3(F) right, and FIG. 3(G) right show the z component of the magnetic field at each of the strongest resonant wavelengths for each of the simulations, and at each of these wavelengths, we visualize strong bulk mode coupling. Interestingly, the random distribution of nanoparticles also provides a much stronger coupling effect than a single nanoparticle, as the reflection dips corresponding to resonant conditions are considerably larger (4-5 times).

Figure 3H:
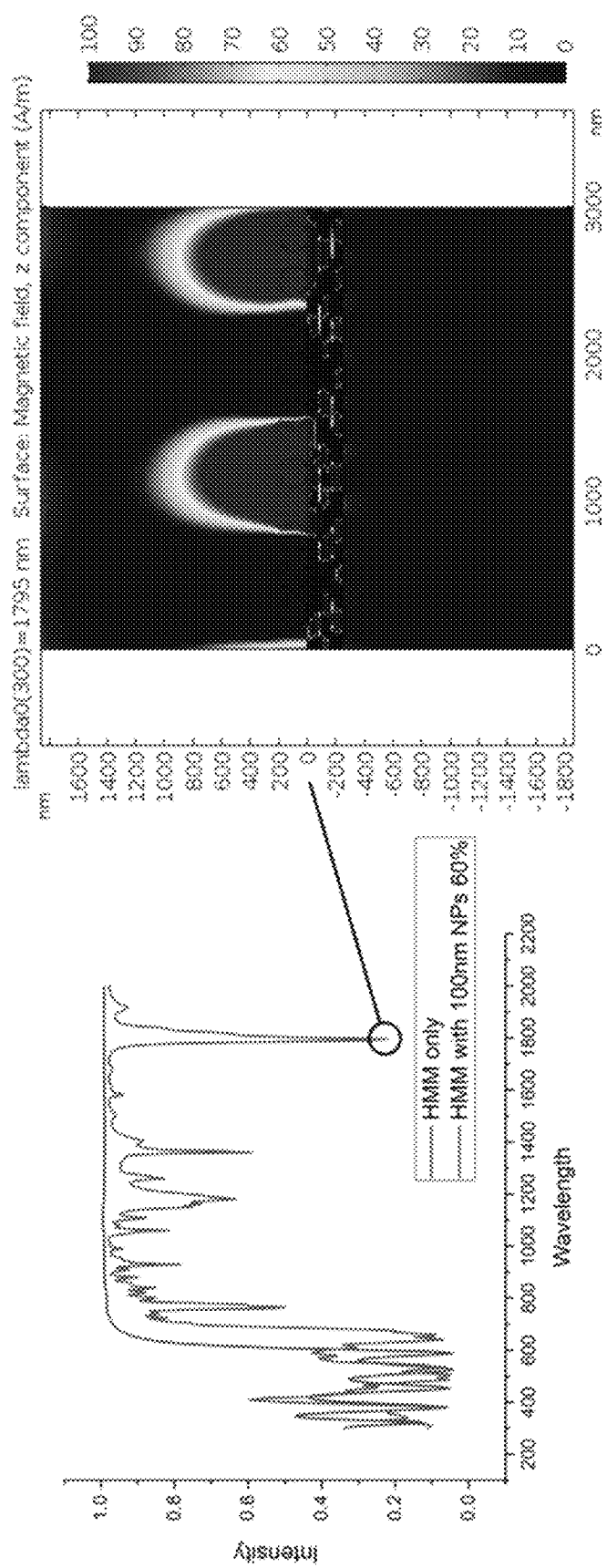

With respect to an HMM exhibiting a randomly dispersed 100 nm $TiO_2$ nanoparticles with 60% coverage, we turn to FIG. 3(H) where we find a much stronger coupling to SPPs and BPPs when compared to just one nanoparticle. As shown in that figure, depicting Hz at 1795 nm, we may see that the period of SPP propagation is slightly larger than that of just 1 nanoparticle—approximately 1500 nm, corresponding to an added momentum of 0.0042 $nm^{-1}$.

Figure 3I:
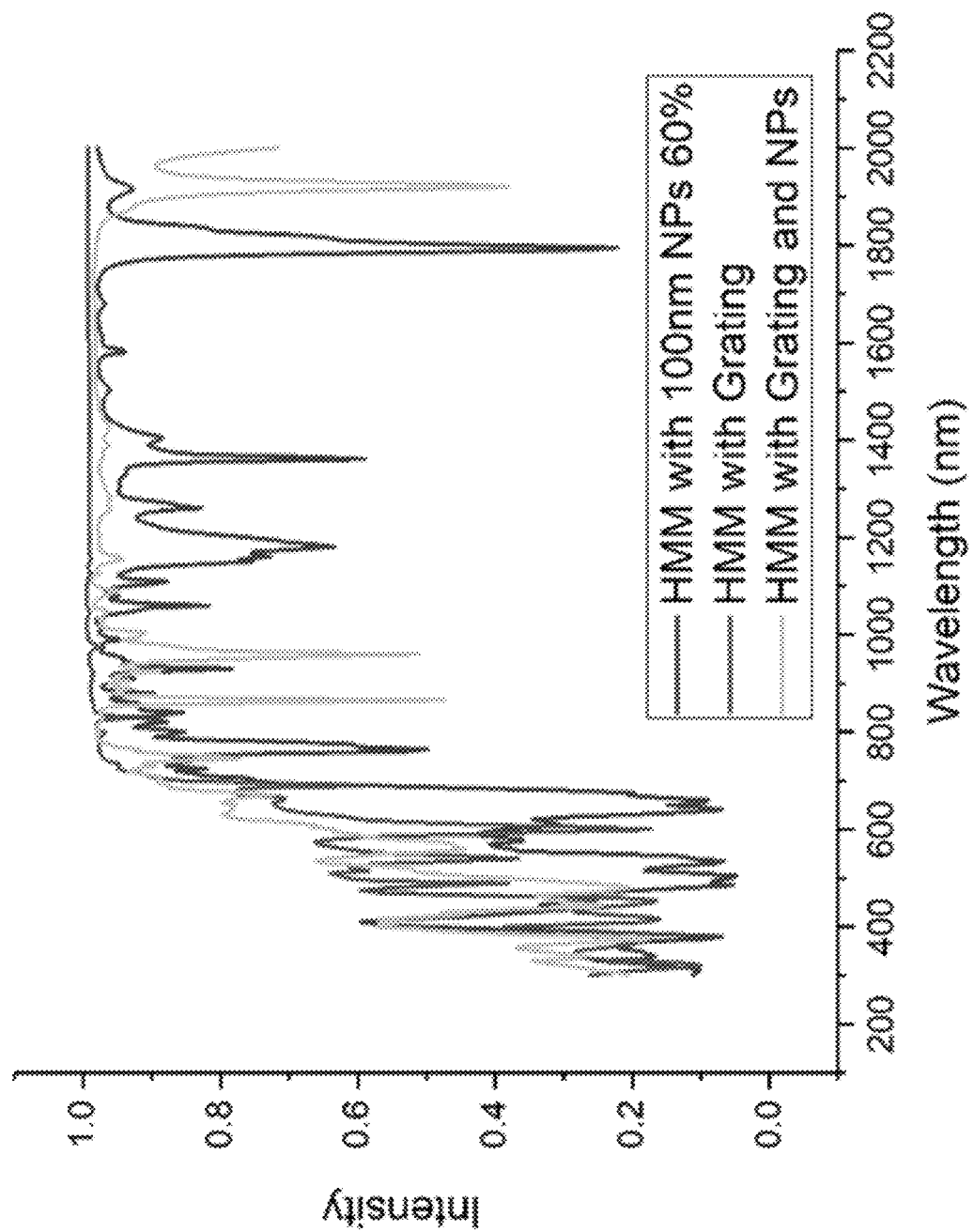
Figure 3J:
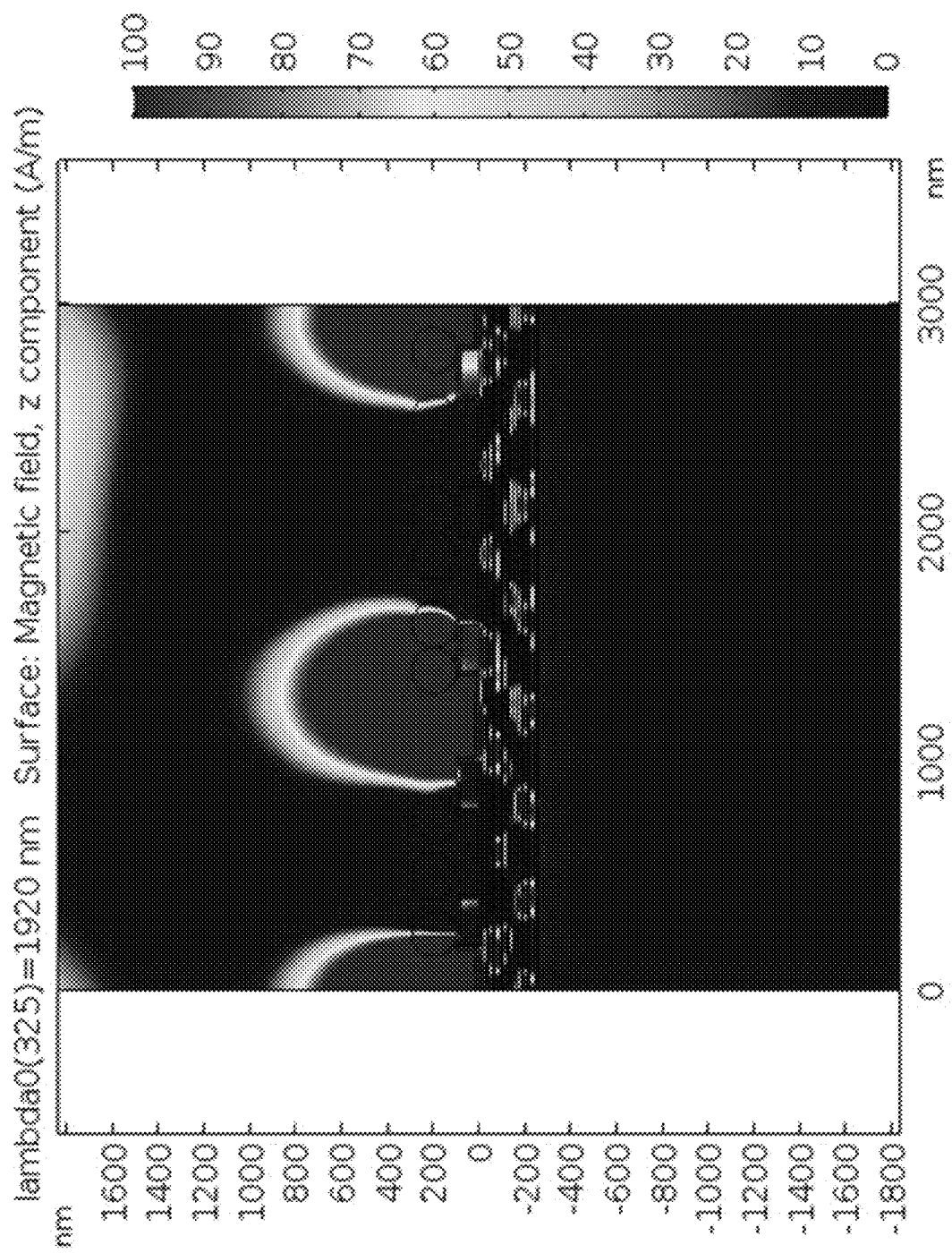

Finally, with respect to a MINI having a randomly dispersed 100 nm $TiO_2$ nanoparticles with 60% linear coverage on a 600 nm Ag grating, we may observe in FIG. 3(I) that reflection spectrum for the MINI with the grating, HMM with grating and nanoparticles, and nanoparticles alone. The random arrangement of the nanoparticles both with the grating and without are identical. The striking feature observed is that the grating suppresses most of the modes caused by the nanoparticles and allows for only discrete sets of large reflection dips. If we further examine the mode around 1915-1920 nm, the quality from the nanoparticles alone is very light. But when we couple to the grating to it, we find it is quite enhanced. The magnetic field plot is shown in FIG. 3(J).

As those skilled in the art will readily appreciate, a planar waveguide can generate an evanescent field that couples incoming incident radiation and a nanostructure. Notwithstanding, it is surprising that random scatters can act as light couplers to an underlying hyperbolic nanostructure. Advantageously, our lithography-free structures require—as their name suggests—no lithography, and therefore may dramatically improve the cost-effectiveness of sensor systems according to the present disclosure relative to grating-based systems.

Figure 4A:
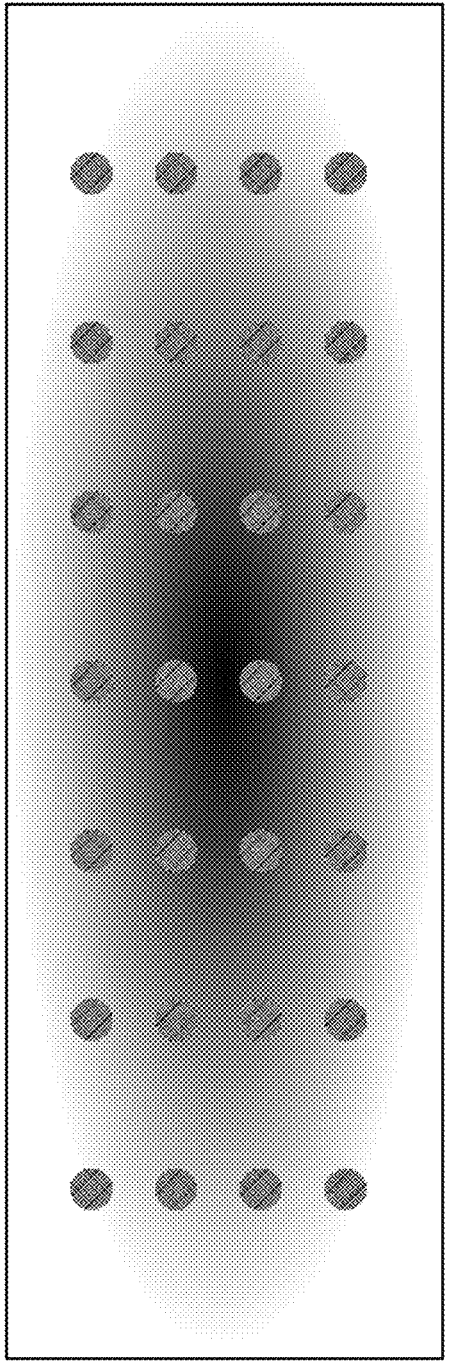
FIGS. 4(A) and 4(B) schematically show a top-view and side-view respectively, of an illustrative alternative embodiment of an HMM sensor device with integrated microfluidic reservoir, channels and filter structures according to an aspect of the present disclosure.
Figure 4B:
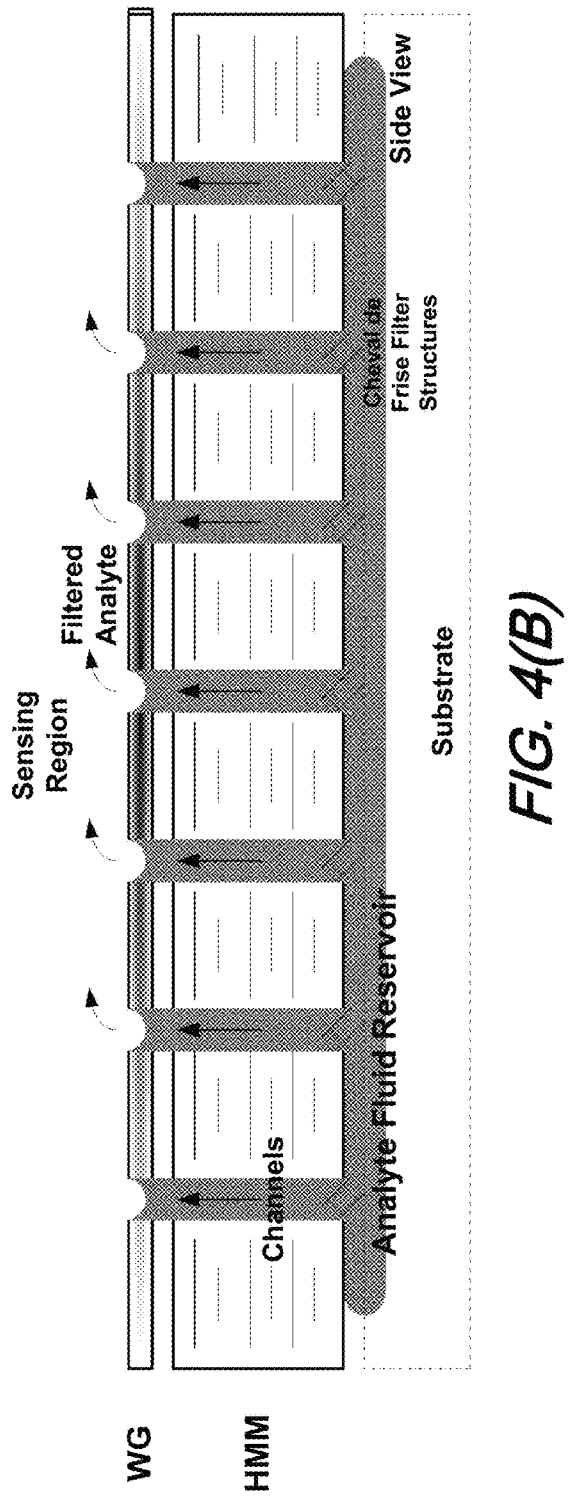

Turning now to FIGS. 4(A) and 4(B), there is shown a top view and side view respectively of yet another alternative embodiment of an HMM sensor structures according to the present disclosure. As may be observed from those figures, a series of channels are nanofabricated across the MINI nanostructure such that an analyte fluid reservoir (shown in the base of a chip) is connected to a sensing area (top superstrate). The substantially cylindrical nanochannel diameter(s) can advantageously range from few tens of nanometers to 500 nm such that a biological sieve is produced thereby filtering large untargeted analytes. More specifically, this filtration may be enhanced by nanostructuring a reticulate "Cheval de Frise"—or alternative structures—at the bottom of the channel.

Figure 5:
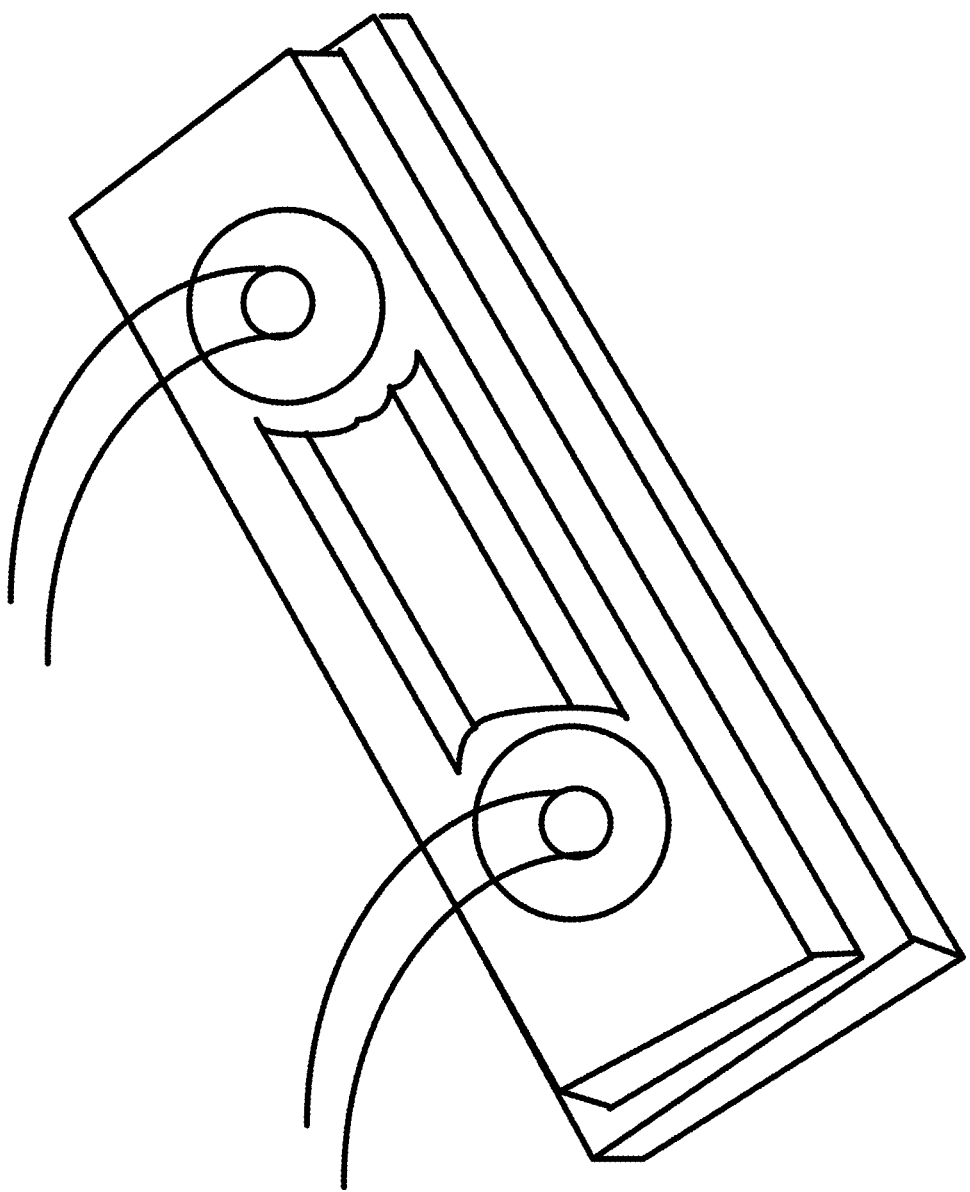
FIG. 5 is a photograph showing the GC-HMM sensor device of FIG. 2 with microfluidic channel and sample tubing according to an aspect of the present disclosure.

FIG. 5 is a photograph of a GC-HMM sensor device according to the present disclosure integrated with a microfluidic channel and sample tubing. As depicted in that FIG. 5, a solution including material(s) to be detected, enters the microfluidic channel from one of the tubes and exits the channel through the other tube. As previously noted, as the solution traverses the channel, it contacts the GC-HMM thereby permitting detection of the solute(s) by the mechanism(s) described above.

Figure 6:
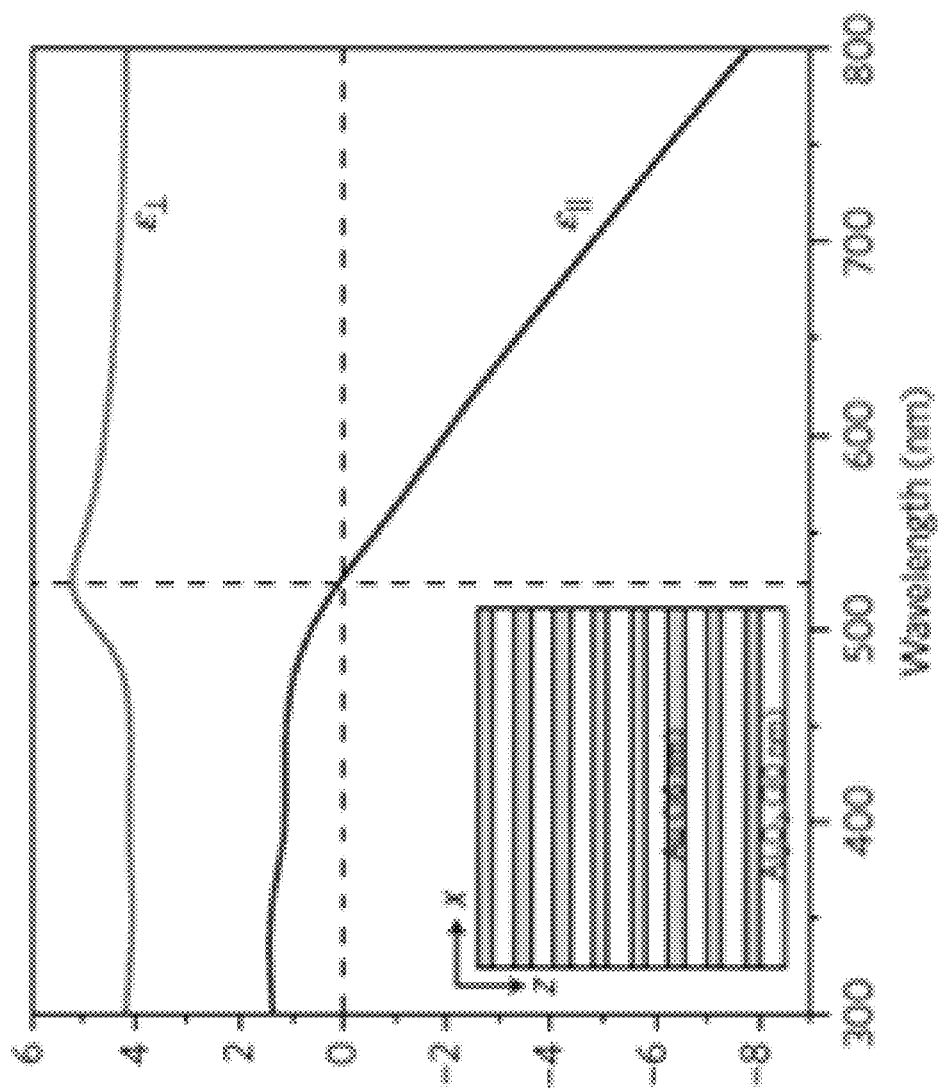
FIG. 6 is a plot showing permittivity of gold/$Al_2O_3$ HMM determined using effective media theory showing a hyperbolic dispersion at 520 nm according to an aspect of the present disclosure.

With reference to FIG. 6, there is shown a plot of permittivity vs. wavelength of Au/Al$_2$O$_3$ HMM determined using effective media theory which shows a hyperbolic dispersion at 520 nm.

Figure 7:
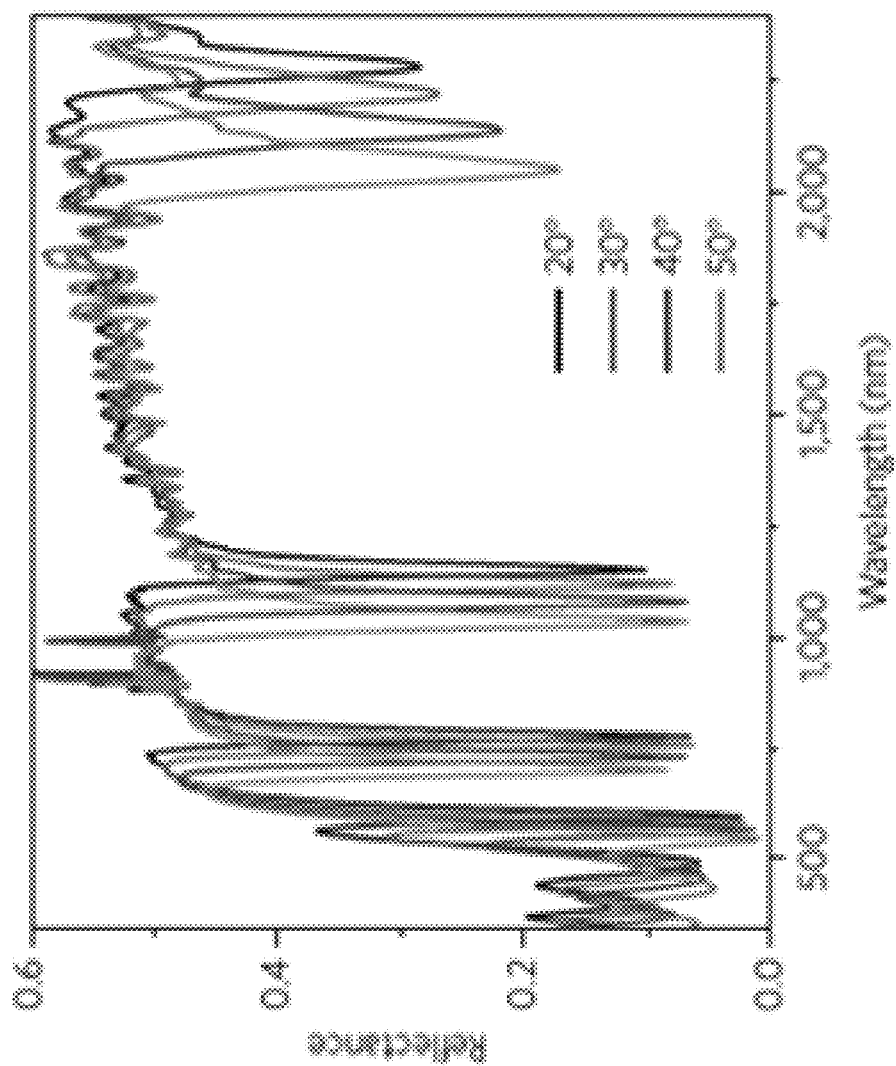
FIG. 7 is a plot showing reflectance spectra of the GC-HMM at different angles of incidence according to an aspect of the present disclosure.

FIG. 7 is a plot showing reflectance vs. wavelength for an illustrative GC-HMM at various angles of incidence. As may be observed from this plot, the GC-HMM sensor structure shows four prominent reflectance dips, corresponding to bulk plasmon polariton modes, and two weak reflectance minima in shorter wavelengths, corresponding to the surface plasmon polariton modes. A blue shift in resonance wavelength with increasing angle of incidence indicates all six modes are guided modes.

At this point, those skilled in the art will readily appreciate that while the methods, techniques and structures according to the present disclosure have been described with respect to particular implementations and/or embodiments, those skilled in the art will recognize that the disclosure is not so limited.

In particular, those skilled in the art will readily appreciate that multiplexing assays (assays that simultaneously measure multiple analytes in a single assay run) are a very important component of contemporary sense and measurement protocols. Of particular significance, sensor structures according to the present disclosure exhibit an inherent multiplexing functionality as they are based in large part on the different sensitivity of the bulk plasmon polariton modes.

Figure 8:
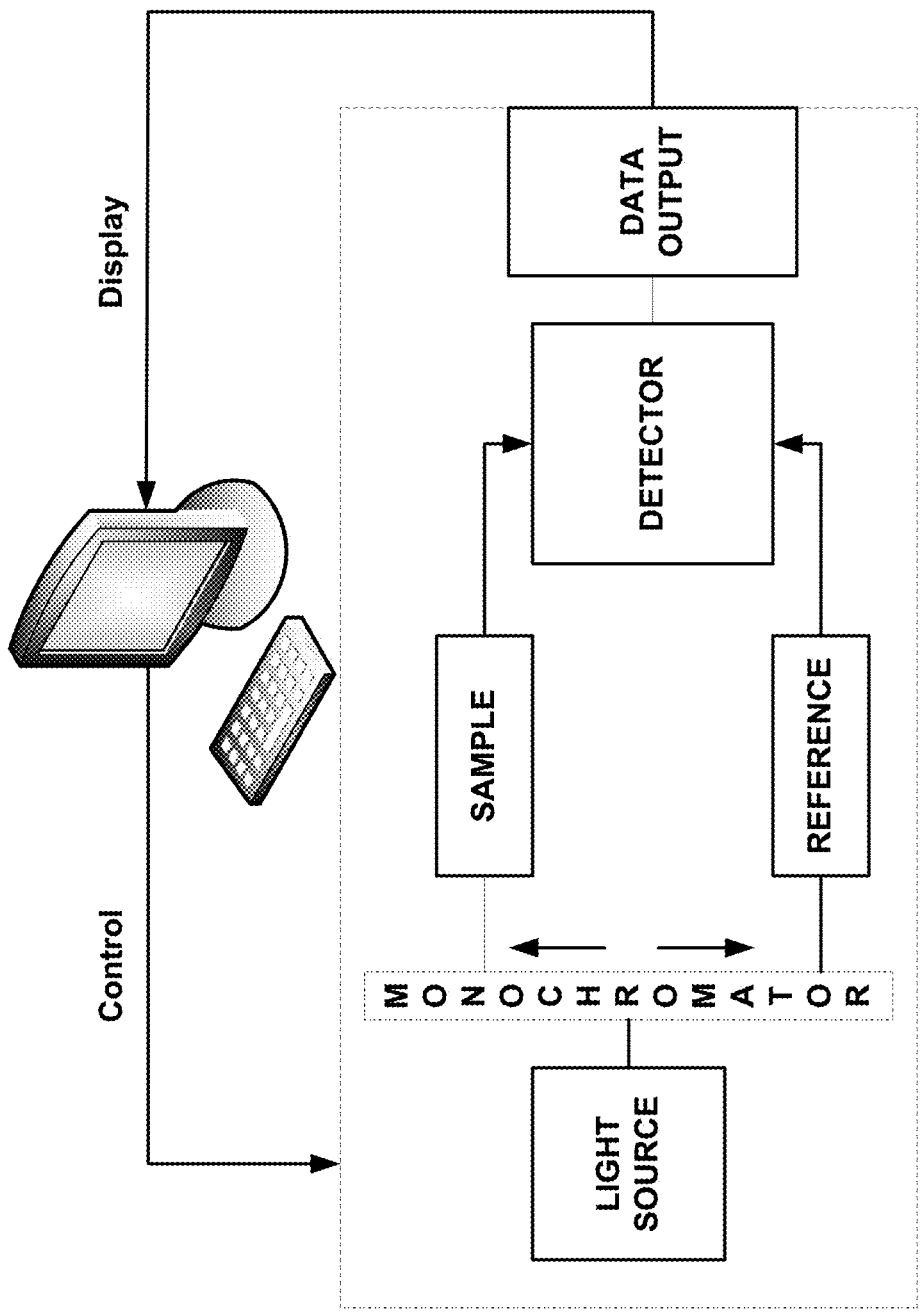
FIG. 8 is a schematic block diagram illustrating the integration of sensor structures according to the present disclosure into higher order instrumentation systems.

More particularly, structures according to the present disclosure simultaneously evaluate an overall wavelength shift of all modes to discriminate binding events of small molecules—which can be detected only from the most sensitive modes—with respect to binding events of large molecules that may be detected by all modes. By exploiting this sensitivity and intrinsic multimodal selective response, sensor structures according to the present disclosure are able to provide an extremely sensitive biosensing platrorm for biological samples—to detect ultra-low molecular weight anaytes. Further theoretical discussion(s) of our HMM sensing structures is provided in the Appendix attached hereto. Lastly, it is noted that structures according to the present disclosure may be advantageously integrated into larger systems (see, e.g., FIG. 8) for detecting analytes. In this manner, analytes detected by the structures according to the present disclosure may be collected, organized, aggregated, and/or reported in an alternative usable form(s). Outputs from such systems would provide—among other things—indicia about the analytes so detected. Accordingly, the scope of the disclosure should only be limited by the claims appended hereto.

The invention claimed is:

1. An optical sensor platform comprising:
a substrate;
an analyte reservoir overlying the substrate;
a hyperbolic metamaterial (HMM) stack overlying the analyte reservoir;
a dielectric overlying the HMM stack; and
an optical structure overlying the dielectric;
wherein the HMM stack, dielectric and optical structure include a number of channels configured to provide fluidic communication between the analyte reservoir and a top portion of the optical structure; and
the sensor platform configured such that when incident optical energy is directed to the HMM via the optical structure a detectable shift in reflected optical energy is produced.

2. The optical sensor platform according to claim 1 wherein the optical structure includes a grating.

3. The optical sensor platform according to claim 1 wherein the optical structure includes a sub-micron layer of methyl methacrylate coated with a layer of metal.

4. The optical sensor platform according to claim 3 wherein the metal coating is substantially 5-15 nm thick.

5. The optical sensor platform according to claim 4 wherein the metal is one selected from the group consisting of Pd, and Pt.

6. The optical sensor platform according to claim 1 wherein the optical structure includes a random distribution of nanoparticles.

7. The optical sensor platform according to claim 6 wherein the random distribution of nanoparticles includes TiO$_2$ nanoparticles exhibiting a diameter of less than 250 nm.

8. The optical sensor platform of claim 7 wherein the nanoparticles provide at least a 60% linear coverage of the dielectric.

9. The optical sensor platform according to claim 1 wherein the optical structure further includes a grating.

* * * * *